(12) United States Patent
Ryu et al.

(10) Patent No.: US 10,881,324 B2
(45) Date of Patent: Jan. 5, 2021

(54) WOUND VOLUME MEASURING METHOD AND DEVICE

(71) Applicant: CG Bio Co., Ltd., Gyeonggi-do (KR)

(72) Inventors: Hyun Seung Ryu, Gyeonggi-do (KR); Joon Pio Hong, Seoul (KR); Jun Hyuk Seo, Gyeonggi-do (KR); Hee Jun Park, Seoul (KR); Soon Gee Hong, Jeollabuk-do (KR); Kang Jin Jeon, Gyeonggi-do (KR); Hoon Kim, Gyeonggi-do (KR)

(73) Assignee: CG Bio Co., Ltd., Gyeonggi-do (KR)

( * ) Notice: Subject to any disclaimer, the term of this patent is extended or adjusted under 35 U.S.C. 154(b) by 142 days.

(21) Appl. No.: 15/549,698

(22) PCT Filed: Jan. 19, 2016

(86) PCT No.: PCT/KR2016/000518
§ 371 (c)(1),
(2) Date: Aug. 9, 2017

(87) PCT Pub. No.: WO2016/129816
PCT Pub. Date: Aug. 18, 2016

(65) Prior Publication Data
US 2018/0042521 A1      Feb. 15, 2018

(30) Foreign Application Priority Data

Feb. 10, 2015   (KR) .................. 10-2015-0020302

(51) Int. Cl.
*A61B 5/00*       (2006.01)
*A61B 5/107*      (2006.01)
(Continued)

(52) U.S. Cl.
CPC .............. *A61B 5/1073* (2013.01); *A61B 5/00* (2013.01); *A61B 5/0055* (2013.01); *A61B 5/107* (2013.01);
(Continued)

(58) Field of Classification Search
CPC ......... A61B 5/00; A61B 5/107; A61B 5/0055; A61B 5/1073; A61B 5/7278; A61B 5/742;
(Continued)

(56) References Cited

U.S. PATENT DOCUMENTS 8,814,841 B2   8/2014  Hartwell
2005/0070858 A1*  3/2005  Lockwood .......... A61F 13/0203
                                                             604/319
(Continued)

FOREIGN PATENT DOCUMENTS

JP     2011-508614 A    3/2011
KR  10-2009-0074188 A   7/2009
(Continued)

OTHER PUBLICATIONS

CL Office Action and Partial Translation of Office Action, dated Aug. 11, 2018, issued by INAPI, Chile.

*Primary Examiner* — Eric J Messersmith
(74) *Attorney, Agent, or Firm* — Hammer & Associates, P.C.

(57) ABSTRACT

The present invention relates to a wound volume measuring method and device, wherein the method comprises the steps of: disposing a foam dressing on a wound site; hermetically sealing the wound site by attaching a film dressing on skin adjacent to the wound site; supplying a negative pressure to the hermetically sealed space formed between the film dressing and the wound site, and thereby discharging fluid into the hermetically sealed space; measuring the flow of the (Continued)

fluid discharged from the hermetically sealed space; and calculating the volume of the wound site on the basis of the measured fluid flow.

7 Claims, 5 Drawing Sheets

(51) Int. Cl.
*A61M 1/00* (2006.01)
*A61F 13/53* (2006.01)
*A61F 13/00* (2006.01)

(52) U.S. Cl.
CPC .............. *A61B 5/445* (2013.01); *A61B 5/742* (2013.01); *A61F 13/53* (2013.01); *A61M 1/0084* (2013.01); *A61M 1/0088* (2013.01); *A61F 2013/00089* (2013.01); *A61F 2013/530802* (2013.01); *A61M 2205/3334* (2013.01)

(58) Field of Classification Search
CPC ....... A61B 5/445; A61B 5/6843; A61F 13/00; A61M 1/0025; A61M 1/0088; A61M 2230/00; A61M 2205/50; A61M 2205/3344; A61M 2205/3331; A61M 2205/18; A61M 2205/15
See application file for complete search history.

(56) References Cited

U.S. PATENT DOCUMENTS

| | | |
|---|---|---|
| 2007/0276309 A1 | 11/2007 | Xu et al. |
| 2011/0178479 A1 | 7/2011 | Perkins et al. |
| 2015/0032031 A1* | 1/2015 | Hartwell ................ A61B 5/107 |
| | | 600/587 |

FOREIGN PATENT DOCUMENTS

| | | |
|---|---|---|
| WO | WO 2009/098696 A2 | 8/2009 |
| WO | WO 2014-053232 A1 | 4/2014 |

\* cited by examiner

WOUND VOLUME MEASURING METHOD AND DEVICE

TECHNICAL FIELD

The present invention relates to a wound treatment device, and more particularly, to a wound volume measuring method and device for measuring a wound volume for wound treatment.

BACKGROUND ART

In the hospital, the treatment using a negative pressure has been performed to promote treatment of a wound site. In order to treat the wound site using the negative pressure, a porous pad or the like is first attached to the wound site. Exudates generated at the wound site are absorbed by the porous pad attached to the wound site.

A suction head is connected to the porous pad or the like, and the suction head is connected to a vacuum device (i.e., an aspirator) through a drain tube or the like. When the negative pressure is generated in the vacuum device, the negative pressure is transmitted to the suction head.

As the negative pressure is transmitted to the suction head, the suction head sucks the exudates absorbed on the porous pad or the like. The exudates sucked by the suction head are discharged to the outside through the drain tube.

Then, wound healing can be promoted through an irrigation unit in which a separate therapeutic substance is administered to the wound site from which the exudates are discharged.

It is preferred that the therapeutic substance is administered so as to correspond to the volume of the wound site. However, the size of the wound site varies depending on the individual patient, so that the dose of the therapeutic substance cannot be determined uniformly.

In addition, since the wound is hermetically sealed with a film dressing while being filled with the porous pad, it is difficult to estimate the volume of the wound site from the outside. Now, the physician is determining the dose of the therapeutic substance based on experience and the patient's improvement.

PRIOR ART DOCUMENT

Patent Document

Patent Document 1) Korean Laid-Open Patent Publication No. 10-2011-0062962 (published on Jun. 10, 2011)

DISCLOSURE

Technical Problem

It is an object to be solved by the present invention to provide a wound volume measuring method and device capable of promoting the wound treatment by measuring the volume of the wound.

The objects of the present invention are not limited to the above-mentioned objects, and other objects not mentioned can be clearly understood by those having ordinary skill in the art to which the present invention belongs from the following description.

Technical Solution

To achieve the object, the wound volume measuring method according to an embodiment of the present invention comprises steps of disposing a foam dressing on a wound site; hermetically sealing the wound site by attaching a film dressing to skin adjacent to the wound site; supplying a negative pressure to the hermetically sealed space formed between the film dressing and the wound site to discharge fluid in the hermetically sealed space; measuring the flow of the fluid discharged from the hermetically sealed space; and calculating the volume of the wound site on the basis of the measured fluid flow.

In some embodiments, the step of calculating the volume of the wound site may calculate the volume of the wound site by integrating the flow of the fluid discharged in the process that the film dressing and the foam dressing are compressed onto the surface of the wound site.

In some embodiments, the step of calculating the volume of the wound site may calculate the volume of the wound site by integrating the flow of the fluid measured from the time when the measured flow change rate of the fluid exceeds the critical change rate.

In some embodiments, the step of calculating the volume of the wound site may calculate the volume of the wound site by integrating the flow of the fluid measured from the time when the measured flow of the fluid becomes smaller than the critical flow.

In some embodiments, the step of calculating the volume of the wound site may calculate the volume of the wound site by integrating the flow of the fluid measured until the negative pressure in the hermetically sealed space corresponds to the critical negative pressure.

In some embodiments, the method may further comprise a step of displaying the calculated volume of the wound site.

To achieve the object, the wound volume measuring device according to an embodiment of the present invention comprises a foam dressing disposed on a wound site; a film dressing attached to skin adjacent to the wound site to hermetically seal the wound site; a drain tube whose one end is in communication with a hermetically sealed space formed between the film dressing and the wound site; a negative pressure generating unit connected to the other end of the drain tube and supplying a negative pressure to the hermetically sealed space; a flow sensor for measuring a flow of fluid discharged from the hermetically sealed space by the negative pressure; and a volume calculating part for calculating a volume of the wound site based on the flow of the fluid measured in the flow sensor.

In some embodiments, the volume calculating part may calculate the volume of the wound site by integrating the flow of the fluid discharged in the process that the film dressing and the foam dressing are compressed onto the surface of the wound site.

In some embodiments, the volume calculating part may calculate the volume of the wound site by integrating the flow of the fluid measured from the time when the measured flow change rate of the fluid exceeds the critical change rate.

In some embodiments, the volume calculating part may calculate the volume of the wound site by integrating the measured flow of the fluid from the time when the measured flow of the fluid becomes smaller than the critical flow.

In some embodiments, the volume calculating part may calculate the volume of the wound site by integrating the flow of the fluid measured until the negative pressure in the hermetically sealed space corresponds to the critical negative pressure.

In some embodiments, the device may further comprise a canister connected to the drain tube to receive fluid discharged from the hermetically sealed space by a negative pressure.

In some embodiments, the device may further comprise a display part for displaying the volume of the wound calculated by the volume calculating part.

The details of other embodiments are included in the detailed description and drawings.

Advantageous Effects

According to the wound volume measuring method and device of the present invention, there is one or more of the following effects.

The volume of the wound can be measured automatically. Furthermore, based on the volume of the wound automatically measured, there is an effect capable of more accurately determining the dose of the therapeutic substance to be administered into the wound.

The effects of the present invention are not limited to the effects mentioned above, and other effects not mentioned can be clearly understood by those skilled in the art from the description of the claims.

BEST MODE

The advantages and features of the present invention and the method of achieving them will become apparent with reference to embodiments as described in detail below together with the accompanying drawings. However, the present invention is not limited to embodiments disclosed below, but may be embodied in many different forms, where these embodiments make the disclosure of the present invention complete and are provided to completely inform those skilled in the art the scope of the invention, and the present invention is only defined by the scope of the claims. The same reference numerals refer to the same components throughout the specification.

The terms used herein are for explaining embodiments and do not limit the present invention. In this specification, the singular forms also include plural forms unless otherwise specified. As used herein, the term "comprises" and/or "comprising" does not exclude the presence or addition of one or more other components, steps, operations and/or elements, in addition to the mentioned components, steps, operations and/or elements.

Unless otherwise defined, all terms (including technical and scientific terms) used herein may be used in a sense commonly understood by those having ordinary skill in the art to which the present invention belongs. Also, the terms defined in commonly used dictionaries are not ideally or excessively interpreted, unless explicitly defined in particular.

Hereinafter, the present invention will be described by embodiments of the present invention with reference to the drawings for explaining the wound volume measuring device.

Figure 1:
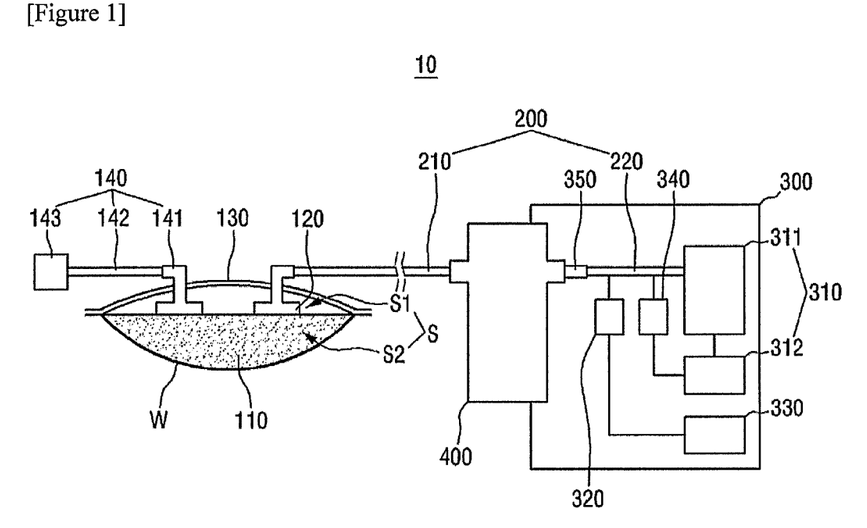
FIG. 1 is a schematic view showing the wound volume measuring device according to one embodiment of the present invention.

FIG. 1 is a schematic view showing the wound volume measuring device according to one embodiment of the present invention.

Referring to FIG. 1, the wound volume measuring device (10) according to one embodiment of the present invention comprises a foam dressing (110), a suction head (120), a film dressing (130), an irrigation unit (140), a drain tube (200), a housing (300), a negative pressure generating unit (310), a flow sensor (320), a volume calculating part (330), a pressure sensor (340), a hydrophobic filter (350) and a canister (400).

As shown in FIG. 1, the foam dressing (110) is disposed in a depressed wound site (W). The foam dressing (110) serves to absorb exudates generated in the wound by being disposed in the depressed wound site (W).

The foam dressing (110) may be made of a material such as polyurethane and polyether, in order to efficiently absorb exudates generated from the wound, but is not limited thereto and a material capable of effectively absorbing exudates is sufficient.

In addition, the foam dressing (110) can be varied in volume by the negative pressure supplied from the negative pressure generating unit (310). For example, as described below, the foam dressing (110) is disposed in the hermetically sealed space (S) between the film dressing (130) and the wound site (W), and when the negative pressure is supplied into the hermetically sealed space (S), the foam dressing (110) is compressed onto the surface of the wound site (W) with the volume reduced. Accordingly, the foam dressing (110) can be varied in volume by the negative pressure.

The film dressing (130) is attached to skin adjacent to the wound site (W) and functions to hermetically seal the wound site (W). As shown in FIG. 1, the film dressing (130) hermetically seals the wound site (W) except for a part of the suction head (120). Accordingly, the hermetically sealed space (S) is formed between the film dressing (130) and the wound site (W). In addition, by being made of a material having elasticity, the film dressing (130) is configured to maintain sealing against the wound site (W) even in an environment where a negative pressure acts in the hermetically sealed space (S) or a negative pressure changes.

The suction head (120) is disposed on one side of the foam dressing (110). The suction head (120) serves to guide the exudates absorbed in the foam dressing (110) to the drain tube (200) by the negative pressure.

The suction head (120) comprises a roughly circular flange part (not numbered) and a connecting tube part (not numbered) connected to the drain tube (200). In the flange part (not numbered), a communicating hole (not shown) in communication with the connecting tube part (not numbered) is formed. Furthermore, in the flange part (not numbered), a plurality of guide flow channels (not shown) whose one end is connected to the communicating hole (not shown) is formed.

The plurality of guide flow channels (not shown) may be radially arranged around the communicating hole (not shown). The plurality of guide flow channels (not shown) serves to guide the exudates absorbed by the foam dressing (110) to the communicating hole (not shown) so as not to be mixed with each other. Accordingly, the exudates absorbed by the foam dressing (110) can be collected into a communicating hole (not shown).

One end of the connecting tube part (not numbered) is in communication with one end of the drain tube (200), and the other end of the connecting tube part (not numbered) is in communication with the communicating hole (not shown) of the flange part (not numbered).

The suction head (120) is disposed in the hermetically sealed space (S) except for the connecting tube part (not numbered).

The drain tube (200) is in communication with the hermetically sealed space (S) formed between the film dressing (130) and the wound site (W) through the suction head (120). For example, by connecting one end of the drain tube (200) to the connecting tube part (not numbered) of the suction head (120), it can be in indirect communication with the hermetically sealed space (S).

However, in certain embodiments, the suction head (120) may be omitted, and one end of the drain tube (200) may be disposed directly in the hermetically sealed space (S) to be in communication with the hermetically sealed space (S).

The drain tube (200) comprises a first tube (210) connecting between the hermetically sealed space (S) and the canister (400), and a second tube (220) connecting between the canister (400) and the negative pressure generating unit (310). In addition, the second tube (220) may be provided with the hydrophobic filter (350).

The hydrophobic filter (350) does not pass any liquid among the fluid flowing in the drain tube (200) and passes only the gas. Accordingly, the hydrophobic filter (350) serves to prevent the liquid (including exudates) from flowing into the negative pressure generating unit (310) through the drain tube (200). Since the liquid such as the exudates does not flow into the negative pressure generating unit (310) by the hydrophobic filter (350), the negative pressure generating unit (310) does not cause failure and/or contamination due to inflow of liquids or the like.

The negative pressure generating unit (310) serves to supply a negative pressure into the hermetically sealed space (S) through the drain tube (200) by generating the negative pressure. The negative pressure generating unit (310) comprises a negative pressure motor (311) for generating a negative pressure and a motor control part (312) for controlling the negative pressure motor (311).

The negative pressure motor (311) serves to generate a negative pressure under the control of the motor control part (312). The negative pressure motor (311) can generate the negative pressure in a plurality of modes by the motor control part (312). In addition, the negative pressure generated by the negative pressure motor (311) is supplied to the hermetically sealed space (S) through the drain tube (200).

The motor control part (312) serves to control the negative pressure motor (311) and feedback-controls the negative pressure motor (311) based on the pressure value in the hermetically sealed space (S) measured by the pressure sensor (340) as described below. For example, when the pressure value measured by the pressure sensor (340) corresponds to a predetermined first critical value, the motor control part (312) can stop driving the negative pressure motor (311), and when the pressure value measured by the pressure sensor (340) corresponds to a predetermined second critical value, the motor control part (312) can drive the negative pressure motor (311).

The pressure sensor (340) is disposed on the drain tube (200) to measure the pressure in the drain tube (200). For example, the pressure sensor (340) may be disposed on the second tube (220) to measure the pressure within the second tube (220). Here, the drain tube (200) and the hermetically sealed space (S) between the film dressing (130) and the wound site (W) form a connected space. Therefore, the pressure in the hermetically sealed space (S) can be grasped by the pressure information in the drain tube (200).

The pressure sensor (340) transmits the measured pressure information to the motor control part (312) and, as described above, the motor control part (312) feedback-controls the negative pressure motor (311) based on the pressure information in the hermetically sealed space (S) measured by the pressure sensor (340).

The flow sensor (320) serves to measure the flow of the fluid discharged from the hermetically sealed space by the negative pressure. The flow sensor (320) may be disposed on the drain tube (200). For example, the flow sensor (320) is disposed on the second tube (220) connecting between the canister (400) and the negative pressure generating unit (310). Preferably, it is disposed between the hydrophobic filter (350) disposed on the second tube (220) and the negative pressure generating unit (310). Accordingly, the flow sensor (320) measures the flow of the fluid flowing in the second tube (220).

The fluid discharged from the hermetically sealed space (S) by the negative pressure comprises gases and/or liquids in the hermetically sealed space (S). The liquid in the hermetically sealed space (S) may comprise exudates generated in the wound site (W). The fluid discharged from the hermetically sealed space (S) flows into the canister (400) through the first tube (210). The liquid in the fluid flowing into the canister (400) is received in the canister (400) by gravity and the gas flows into the second tube (220) by the negative pressure.

Accordingly, the flow sensor (320) disposed on the second tube (220) can measure the flow of the gas in the hermetically sealed space (S) and the flow information measured in the flow sensor (320) is transmitted to the volume calculating part (330).

The volume calculating part (330) serves to automatically calculate the volume of the wound site (W) based on the flow of the fluid measured by the flow sensor (320). The volume of the wound (W) calculated by the volume calculating part (330) serves to determine the amount of the therapeutic substance to be administered to the wound.

The volume calculating part (330) can calculate the volume of the wound site (W) by integrating the flow of the fluid discharged in the process that the film dressing (130) and the foam dressing (110) are compressed onto the surface of the wound site (W). In addition, the volume calculating part (330) can calculate the volume of the wound site by integrating the flow of the fluid measured until the negative pressure in the hermetically sealed space (S) corresponds to the critical negative pressure. The details of the volume calculating part (330) will be described below.

The display part (not shown) serves to display the volume of the wound (W) calculated by the volume calculating part (330), by visually expressing texts and/or images. In addition, the display part (not shown) may also display the dose of the therapeutic substance, the flow measured by the flow sensor (320), the operation state of the negative pressure generating unit (310), and the like.

The canister (400) is disposed on the drain tube (200) and serves to receive a part of the fluid discharged from the hermetically sealed space (S) through the drain tube (200). Some of the fluid received in the canister (400) is mostly composed of liquids (including exudates). In addition, the canister (400) is detachably coupled to one side of the housing (300).

For example, when the negative pressure is supplied to the hermetically sealed space (S), the fluid in the hermetically sealed space (S) is discharged out of the hermetically sealed space (S) through the drain tube (200). The fluid flowing in the drain tube (200) reaches the canister (400) disposed on the drain tube (200). The liquid (including exudates) in the fluid reaching the canister (400) is received into the canister (400) by gravity.

The housing (300) forms an internal space. As shown in FIG. 1, the internal space of the housing (300) receives the negative pressure generating unit (310), a part of the drain tube (200), the hydrophobic filter (350), the pressure sensor (340), the flow sensor (320) and the volume calculating part (330), and the like. Accordingly, the housing (300) functions to protect the configurations accommodated in the inner space from the outside.

A structure with a detachable canister (400) may be provided on one side of the housing (300). In addition, a display part (not shown) may be provided on the outer surface of the housing (300).

The irrigation unit (140) serves to administer the therapeutic substance to the wound site (W).

The irrigation unit (140) comprises an irrigation head (141) disposed on one side of the foam dressing (110), an irrigation tube (142) whose one end is connected to the irrigation head (141) and a therapeutic substance supply part (143) connected to the other end of the irrigation tube (142) and supplying the therapeutic substance to the wound site.

The therapeutic substance supply part (143) receives the therapeutic substance, and the dose of the therapeutic substance can be adjusted by the user's manipulation.

Figure 2:
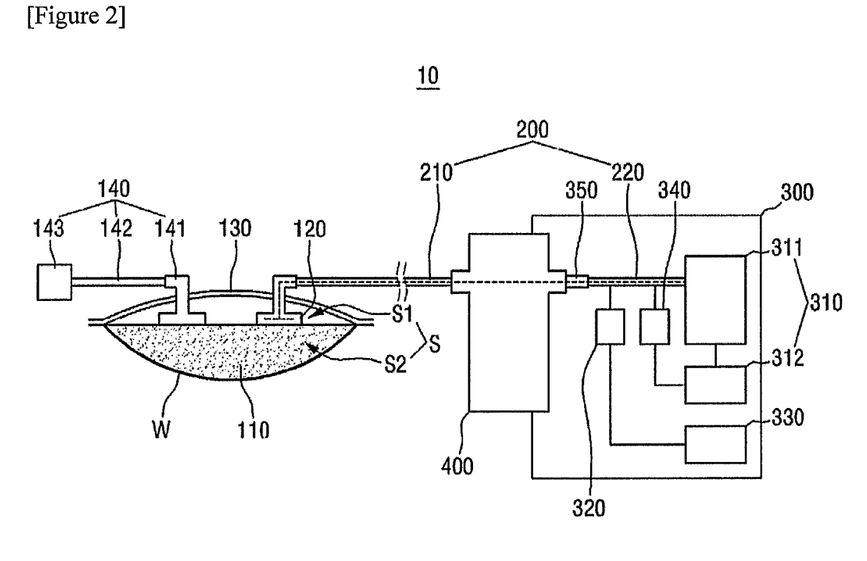
FIGS. 2 to 4 are views for explaining operation of the wound volume measuring device according to one embodiment of the present invention.
Figure 3:
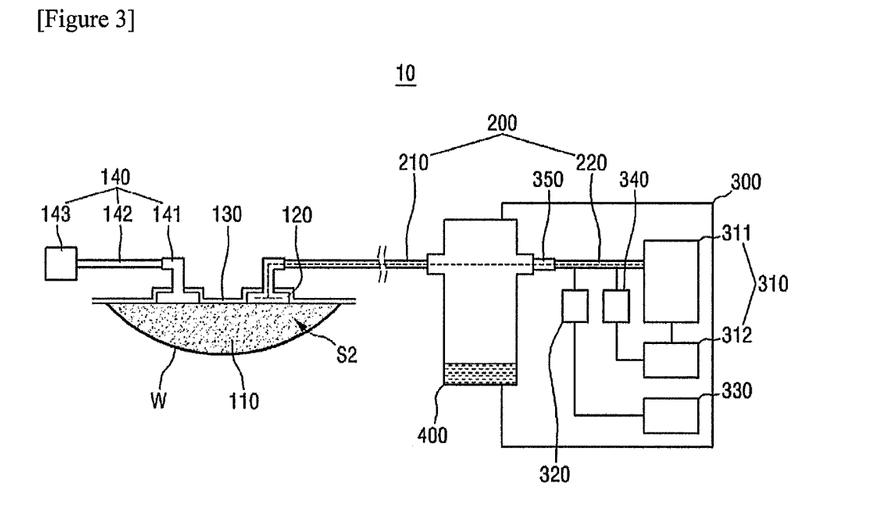
Figure 4:
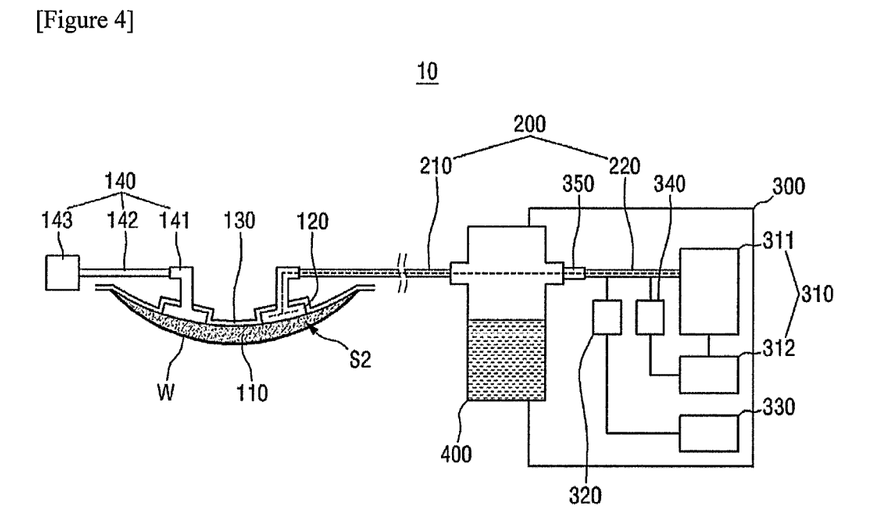

FIGS. 2 to 4 are views for explaining operation of the wound volume measuring device according to one embodiment of the present invention.

Referring to FIGS. 2 to 4, a process of calculating the volume of a wound in the volume calculating part (330) of the wound volume measuring device (10) according to one embodiment of the present invention will be described.

The negative pressure generating unit (310) is driven in a state in which the wound site (W) is hermetically sealed by the film dressing (130). The negative pressure generated in the negative pressure generating unit (310) is supplied to the hermetically sealed space (S) between the film dressing (130) and the wound site (W). The fluid in the hermetically sealed space (S) is discharged by the negative pressure supplied to the hermetically sealed space (S).

As shown in FIG. 2, the hermetically sealed space (S) comprises a first hermetically sealed space (S1) between the film dressing (130) and the foam dressing (110) and a second hermetically sealed space (S2) of the wound site (W) on which the foam dressing (110) is disposed.

In addition, most of the fluid in the first hermetically sealed space (S1) is filled with gases, and the fluid in the second hermetically sealed space (S2) is filled with gases and liquids (including exudates). Furthermore, the second hermetically sealed space (S2) is formed so as to be approximately close to the volume of the wound (W).

As the negative pressure is supplied to the hermetically sealed space (S), the fluid in the first hermetically sealed space (S1) is discharged quickly. Accordingly, the flow measured by the flow sensor (320) is largely measured.

As shown in FIG. 3, as the negative pressure is continuously supplied into the hermetically sealed space (S), the fluid in the first hermetically sealed space (S1) is continuously discharged to reduce the first hermetically sealed space (S1), and finally, the hermetically sealed space (S1) is disappeared. In other words, as the film dressing (130) is compressed onto the foam dressing (110), the first hermetically sealed space (S1) is disappeared.

As shown in FIG. 4, even after the film dressing (130) is compressed onto the foam dressing (110), the negative pressure is continuously supplied into the hermetically sealed space (S). Thus, the film dressing (130) and the foam dressing (110) are compressed onto the surface of the wound site (W). That is, the foam dressing (110), to which the film dressing (130) is compressed, is compressed onto the surface of the wound site (W).

The fluid in the second hermetically sealed space (S2) is discharged in the process that the foam dressing (110), to which the film dressing (130) is compressed, is compressed onto the surface of the wound site (W). In this case, the fluid in the second hermetically sealed space (S2) is discharged slowly, because the fluid in the second hermetically sealed space (S2) is discharged while pressing the foam dressing (110), to which the film dressing (130) is compressed, by the negative pressure. Accordingly, the flow measured by the flow sensor (320) is measured small.

In addition, as described above, the second hermetically sealed space (S2) is formed to be close to the volume of the wound site. Accordingly, when the flow of the fluid discharged in the process that the film dressing (130) and the foam dressing (110) are compressed onto the surface of the wound site (W) is integrated, the volume calculating part (330) can calculate the volume of the wound site (W).

Figure 5:
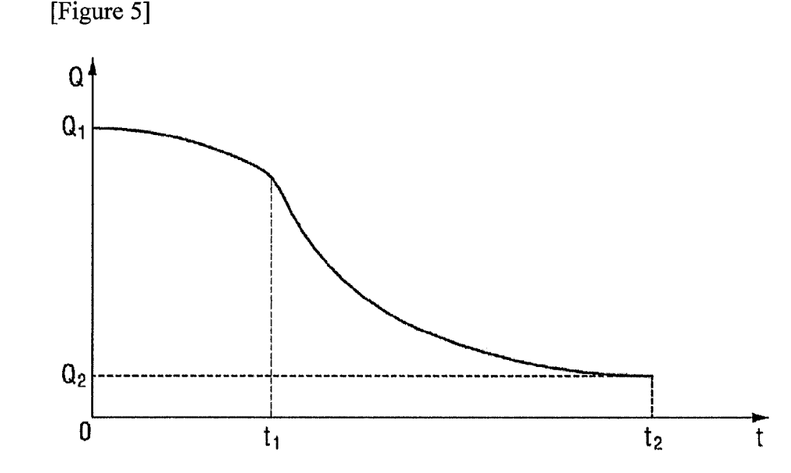
FIG. 5 is a graph schematically showing flow of the fluid generated when the wound volume measuring device according to one embodiment of the present invention is operated.

FIG. 5 is a graph schematically showing flow of the fluid generated when the wound volume measuring device according to one embodiment of the present invention is operated.

Referring to FIG. 5, when the negative pressure is supplied into the hermetically sealed space (S, see FIG. 1), the flow of the fluid discharged in the process (0 to t1) that the film dressing (130, see FIG. 1) is compressed onto the foam dressing (110, see FIG. 1) is formed to be larger than the flow of the fluid discharged in the process (t1 to t2) that the film dressing (130) and the foam dressing (110) are compressed onto the surface of the wound site (W, see FIG. 1).

As described above, since most of the fluid discharged in the process (0 to t1) that the film dressing (130) is compressed onto the foam dressing (110) is not only composed of gases, but also only the tensile force of the film dressing (130) acts as the resistance of the negative pressure, the flow (Q1) of the fluid discharged from the hermetically sealed space (S) is formed to be largest at the beginning.

As shown in FIG. 5, the flow of the fluid discharged in the process (0 to t1) that the film dressing (130) is compressed onto the foam dressing (110) gradually decreases over time. This is because the more the film dressing (130) is compressed onto the foam dressing (110), the tensile force of the film dressing (130) which acts as the resistance of negative pressure increases.

Accordingly, the flow of the fluid discharged in the hermetically sealed space (S) gradually decreases. However, the flow change rate of the fluid is formed to be smaller than the critical change rate.

After the film dressing (130) is compressed onto the foam dressing (110), the film dressing (130) and the foam dressing (110) are compressed onto the surface of the wound site (W) by the negative pressure supplied in the hermetically sealed space (S). In other words, the foam dressing (110), to which the film dressing (130) is compressed, is compressed onto the surface of the wound site (W).

The flow of the fluid discharged in the process (t1 to t2) that the film dressing (130) and the foam dressing (110) are compressed onto the surface of the wound site (W) is formed to be smaller than the flow of the fluid discharged in the process (0 to t1) that the film dressing (130) is compressed onto the foam dressing (110).

As described above, the fluid discharged in the process (t1 to t2) that the film dressing (130) and the foam dressing (110) are compressed onto the surface of the wound site (W) is not only composed of liquids (including exudates) and gases, but also the tensile force of the film dressing (130) and the compression force of the foam dressing (110) act as the resistance of the negative pressure.

Accordingly, the flow of the fluid discharged in the process (t1 to t2) that the film dressing (130) and the foam dressing (110) are compressed onto the surface of the wound site (W) is formed to be smaller than the flow of the fluid discharged in the process (0 to t1) that the film dressing (130) is compressed onto the foam dressing (110).

Also, the smallest flow (Q2) of the fluid is measured in the process (t1 to t2) that the film dressing (130) and the foam dressing (110) are compressed onto the surface of the wound site (W).

As shown in FIG. 5, when the tensile force of the film dressing (130) and the compression force of the foam dressing (110) acts as the resistance of the negative pressure, the flow change rate of the fluid discharged from the hermetically sealed space (S) is formed to be larger than the critical change rate. That is, the flow of the fluid discharged from the hermetically sealed space (S) is drastically reduced.

In FIGS. 2 to 4, as described above, the fluid discharged in the process that the film dressing (130) and the foam dressing (110) are compressed onto the surface of the wound site (W) is a fluid discharged from the second hermetically sealed space (S2, see FIG. 1) which is almost close to the volume of the wound.

Therefore, when the flow of the fluid measured from the time (t1) when the measured flow change rate of the fluid exceeds the critical change rate is integrated, the volume calculating part (330) can calculate the volume of the wound site (W).

In addition, when the flow of the fluid measured from the time (t1) when the measured flow change rate of the fluid exceeds the critical change rate until the negative pressure in the hermetically sealed space (S) corresponds to the critical negative pressure is integrated, the volume calculating part (330) can calculate the volume of the wound site (W).

If the absolute value of the negative pressure in the hermetically sealed space (S) is formed to be larger than the absolute value of the critical negative pressure, this is because the wound site in the hermetically sealed space (S) may be damaged by the negative pressure.

Figure 6:
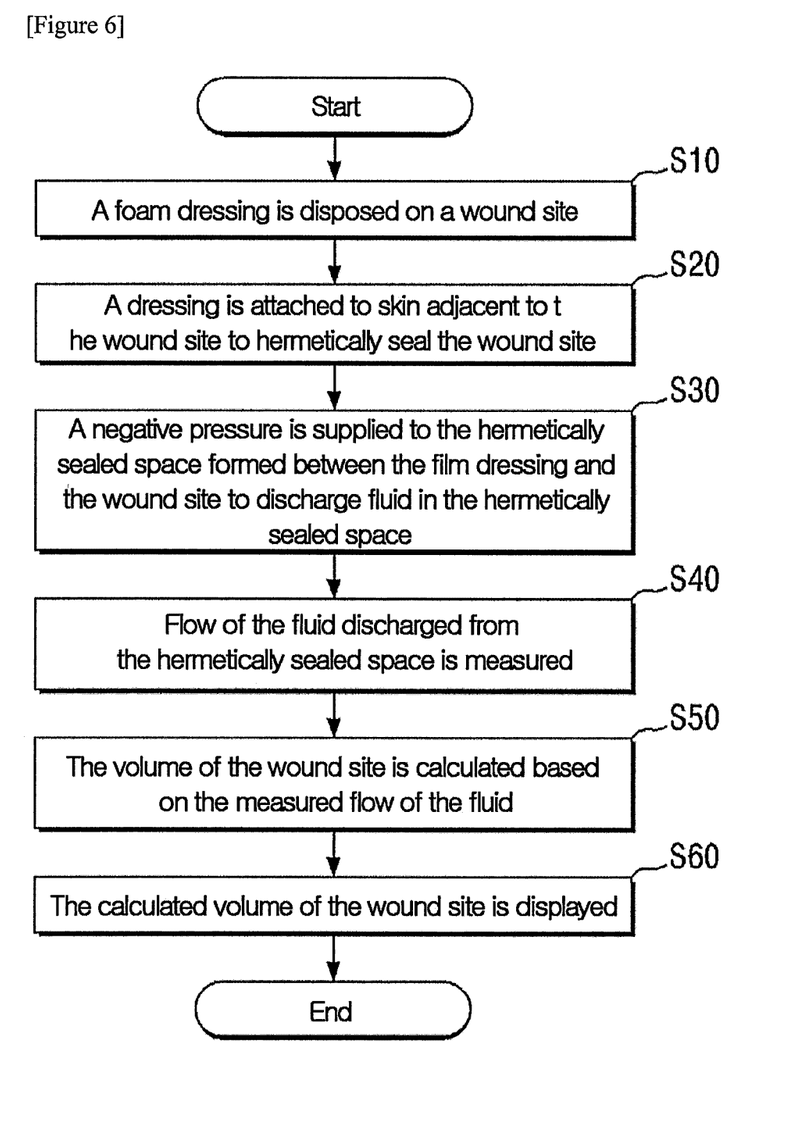
FIG. 6 is a flowchart showing an operation process of the wound volume measuring device according to one embodiment of the present invention.

FIG. 6 is a flowchart showing an operation process of the wound volume measuring device according to one embodiment of the present invention.

Referring to FIG. 6, a process of measuring the volume of the wound using the wound volume measuring device (10, see FIG. 1) of the present invention will be described.

First, the foam dressing (110, see FIG. 1) is disposed on the wound site (W, see FIG. 1) (S11). It is preferred that the foam dressing (110) is formed to substantially correspond to the volume of the wound site (W). The foam dressing (110) disposed on the wound site (W) absorbs exudates generated from the wound.

The suction head (120, see FIG. 2) is disposed on one side of the foam dressing (110), and the film dressing (130, see FIG. 1) is attached to skin adjacent to the wound site (W) to hermetically seal the wound site (W) (S20). As the wound site (W) is hermetically sealed with the film dressing (130), the hermetically sealed space (S, see FIG. 1) is formed between the film dressing (130) and the wound site (W). However, the film dressing (130) hermetically seals the wound site (W) except for the connecting tube part (122, see FIG. 1) of the suction head (120).

The negative pressure is supplied to the hermetically sealed space (S) between the film dressing (130) and the wound site (W) to discharge the fluid in the hermetically sealed space (S) (S30). For example, the negative pressure is supplied to the hermetically sealed space (S) through the drain tube (200, see FIG. 1) connected to the connecting tube part (not numbered) of the suction head (120) to be in communication with the hermetically sealed space (S). As the negative pressure is supplied to the hermetically sealed space (S), the fluid in the hermetically sealed space (S) can be discharged.

The flow of the fluid discharged from the hermetically sealed space (S) is measured (S40). For example, the flow sensor (320, see FIG. 1) measures the flow of the fluid flowing in the drain tube (200).

The volume of the wound site (W) is calculated based on the measured flow of the fluid (S50). For example, the volume calculating part (330, see FIG. 1) calculates the volume of the wound site by integrating the flow of the fluid discharged in the process that the film dressing (130) and the foam dressing (110) are compressed onto the surface of the wound site (W).

In addition, the volume calculating part (330) calculates the volume of the wound site by integrating the flow of the fluid measured from the time when the measured fluid change rate exceeds the critical change rate. The volume calculating part (330) calculates the volume of the wound site (W) by integrating the flow of the fluid measured until the negative pressure in the hermetically sealed space (S) corresponds to the critical negative pressure.

In other words, the volume calculating part (330) calculates the volume of the wound site (W) by integrating the flow of the fluid measured from the time when the measured fluid change rate exceeds the critical change rate until the negative pressure in the hermetically sealed space (S) corresponds to the critical negative pressure.

In certain embodiments, the volume calculating part (330) can calculate the volume of the wound site by integrating the flow of the fluid measured from the time when the measured flow of the fluid becomes smaller than the critical flow until the negative pressure in the hermetically sealed space (S) corresponds to the critical negative pressure.

The calculated volume of the wound site (W) is displayed (S60). For example, the volume of the wound site (W) calculated by the volume calculating part (330) is displayed through the display part (not shown). Accordingly, the user can accurately recognize the volume of the wound site, and can determine the dose of the therapeutic substance to correspond to the volume of the wound site (W).

Figure 7:
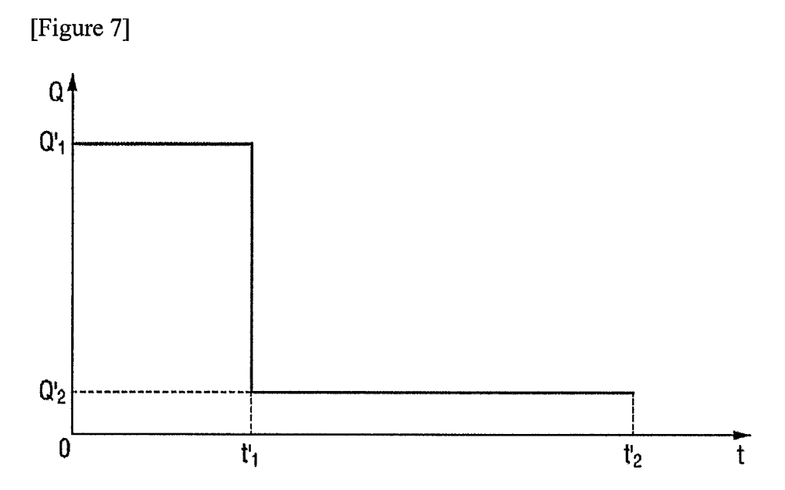
FIG. 7 is a graph schematically showing flow of the fluid generated when the wound volume measuring device according to another embodiment of the present invention is operated.

FIG. 7 is a graph schematically showing flow of the fluid generated when the wound volume measuring device according to another embodiment of the present invention is operated.

Referring to FIG. 7, when the negative pressure is supplied into the hermetically sealed space, the flow (Q'1) of the fluid discharged in the process (0 to t' 1) that the film dressing is compressed onto the foam dressing is formed to be larger than the flow (Q'2) of the fluid discharged in the process (t'1 to t'2) that the film dressing and the foam dressing are compressed onto the surface of the wound site.

As described above, since most of the fluid discharged in the process (0 to t'1) that the film dressing is compressed onto the foam dressing is not only composed of gases, but also the negative pressure uses only the tensile force of the film dressing, the flow (Q'1) of the fluid discharged from the hermetically sealed space is formed to be largest at the beginning.

As shown in FIG. 7, the tensile force of the film dressing which acts as the resistance of the negative pressure due to the attachment state of the film dressing, the size of the wound, and the like can constantly act in the process (0 to t'1) in which the film dressing is compressed onto the foam dressing.

Accordingly, the flow (Q'1) of the fluid discharged in the process (0 to t'1) that the film dressing is compressed onto the foam dressing can be kept approximately constant.

After the film dressing is compressed onto the foam dressing, the film dressing and the foam dressing are compressed onto the surface of the wound site by the negative pressure supplied in the hermetically sealed space. In other words, the foam dressing, to which the film dressing is compressed, is compressed onto the surface of the wound site.

The flow (Q'2) of the fluid discharged in the processes (t'1 to t'2) that the film dressing and the foam dressing are compressed onto the surface of the wound site is formed to be smaller than the flow (Q'1) discharged in the process (0 to t'1) that the film dressing is compressed onto the foam dressing.

As described above, since the fluid discharged in the process (t'1 to t'2) that the film dressing and the foam dressing are compressed onto the surface of the wound site is not only composed of liquids (including exudates) and gases, but also the tensile force of the film dressing and the compression force of the foam dressing act as the resistance of the negative pressure, the flow (Q'2) of the fluid discharged from the hermetically sealed space is formed to be smaller than the flow (Q'1) of the fluid discharged in the process (0 to t'1) that the film dressing is compressed onto the foam dressing.

As shown in FIG. 7, the tensile force of the film dressing caused by the negative pressure and the compressive force of the foam dressing generated by the negative pressure due to the attachment state of the film dressing, the size of the wound, the size of the foam dressing, materials and the like can be kept constant in the process that the film dressing and the foam dressing are compressed onto the surface of the wound site.

Accordingly, the flow (Q'2) of the fluid discharged in the process (t'1 to t'2) that the film dressing and the foam dressing are compressed onto the surface of the wound site can be kept approximately constant.

In FIGS. 2 to 4, as described above, the fluid discharged in the process (t'1 to t'2) that the film dressing and the foam dressing are compressed onto the surface of the wound site is a fluid discharged from the second hermetically sealed space which is almost close to the volume of the wound. Therefore, when the flow of the fluid measured from the time (t'1) when the measured flow of the fluid becomes smaller than the critical flow is integrated, the volume calculating part can calculate the volume of the wound site (W).

In addition, the critical flow can be set to a value between a flow (Q'1) of the fluid discharged in the process (0 to t'1) that the film dressing is compressed onto the foam dressing, and a flow (Q'2) of the fluid discharged in the process (t'1 to t'2)) that the film dressing and the foam dressing are compressed onto the surface of the wound site.

The volume calculating part can calculate the volume of the wound site by integrating the flow of the fluid measured from the time point (t'1) when the measured flow of the fluid becomes smaller than the critical flow until the negative pressure in the hermetically sealed space corresponds to the critical negative pressure.

Hereinbefore, the preferred embodiments of the present invention have been shown and described, but the present invention is not limited to certain embodiments as described above, where various modifications can be made by those having ordinary skill in the art to which the invention belongs without departing from the gist of the invention claimed in the claims as well as these modifications should not be individually understood from technical thoughts or prospects of the present invention.

MODE FOR INVENTION

The wound volume measuring method according to an embodiment of the present invention comprises steps of disposing a foam dressing on a wound site, hermetically sealing the wound site by attaching a film dressing to skin adjacent to the wound site, supplying a negative pressure to the hermetically sealed space formed between the film dressing and the wound site to discharge fluid in the hermetically sealed space, measuring the flow of the fluid discharged from the hermetically sealed space and calculating the volume of the wound site on the basis of the measured fluid flow.

The wound volume measuring device according to an embodiment of the present invention comprises a foam dressing disposed on a wound site, a film dressing attached to skin adjacent to the wound site to hermetically seal the wound site, a drain tube whose one end is in communication with a hermetically sealed space formed between the film dressing and the wound site, a negative pressure generating unit connected to the other end of the drain tube and supplying a negative pressure to the hermetically sealed space, a flow sensor for measuring a flow of fluid discharged from the hermetically sealed space by the negative pressure and a volume calculating part for calculating a volume of the wound site based on the flow of the fluid measured in the flow sensor.

The invention claimed is:

1. A wound volume measuring method comprising steps of:
    disposing a foam dressing on a wound site;
    hermetically sealing said wound site by attaching a film dressing to skin adjacent to said wound site;
    supplying a negative pressure to the hermetically sealed space formed between said film dressing and said wound site to discharge fluid in said hermetically sealed space;
    measuring the flow of said fluid discharged from said hermetically sealed space; and
    calculating the volume of said wound site on the basis of the measured fluid flow,
    wherein the hermetically sealed space comprises a first hermetically sealed space between the film dressing and the foam dressing and a second hermetically sealed space of the wound site on which the foam dressing is disposed,
    wherein when the fluid in the first hermetically sealed space is discharged to reduce the first hermetically sealed space, and the hermetically sealed space is disappeared; the film dressing is compressed onto the foam dressing, wherein even after the film dressing is compressed onto the foam dressing, the negative pressure is continuously supplied into the hermetically sealed space, the film dressing and the foam dressing are compressed onto the surface of the wound site, wherein the step of calculating the volume of said wound site calculates the volume of said wound site by integrating the flow of the fluid discharged in the process that said film dressing and said foam dressing are compressed onto the surface of said wound site, when the negative pressure is supplied into the hermetically sealed space, the flow of the fluid discharged in the process that the film dressing is compressed onto the foam dressing is formed to be larger than the flow of the fluid discharged in the process that the film dressing and the foam dressing are compressed onto the surface of the wound site, wherein the step of calculating the volume of said wound site calculates the volume of said wound site by integrating the flow of said fluid measured from the time when the measured flow of said fluid becomes lower than the critical flow, and wherein the critical flow can be set to a value between a flow of the fluid discharged in the process that the film dressing is compressed onto the foam dressing, and a flow of the fluid discharged in the process that the film dressing and the foam dressing are compressed onto the surface of the wound site.

2. The wound volume measuring method according to claim 1, wherein the step of calculating the volume of said wound site calculates the volume of said wound site by integrating the flow of said fluid measured until the negative pressure in said hermetically sealed space corresponds to a critical negative pressure.

3. The wound volume measuring method according to claim 1, further comprising
   a step of displaying the calculated volume of said wound site.

4. A wound volume measuring device comprising
   a foam dressing disposed on a wound site;
   a film dressing attached to skin adjacent to said wound site to hermetically seal said wound site;
   a drain tube whose one end is in communication with a hermetically sealed space formed between said film dressing and said wound site;
   a negative pressure generating unit connected to the other end of said drain tube and supplying a negative pressure to said hermetically sealed space;
   a flow sensor for measuring a flow of fluid discharged from said hermetically sealed space by said negative pressure; and
   a volume calculating part for calculating a volume of said wound site based on the flow of said fluid measured in said flow sensor, wherein the hermetically sealed space comprises a first hermetically sealed space between the film dressing and the foam dressing and a second hermetically sealed space of the wound site on which the foam dressing is disposed, wherein when the fluid in the first hermetically sealed space is discharged to reduce the first hermetically sealed space, and the hermetically sealed space is disappeared, the film dressing is compressed onto the foam dressing, wherein even after the film dressing is compressed onto the foam dressing, the negative pressure is continuously supplied into the hermetically sealed space, the film dressing and the foam dressing are compressed onto the surface of the wound site, wherein the step of calculating the volume of said wound site calculates the volume of said wound site by integrating the flow of the fluid discharged in the process that said film dressing and said foam dressing are compressed onto the surface of said wound site, when the negative pressure is supplied into the hermetically sealed space, the flow of the fluid discharged in the process that the film dressing is compressed onto the foam dressing is formed to be larger than the flow of the fluid discharged in the process that the film dressing and the foam dressing are compressed onto the surface of the wound site, wherein said volume calculating unit calculates the volume of said wound site by integrating the flow of said fluid measured from the time when the measured flow of said fluid becomes lower than the critical flow, and wherein the critical flow can be set to a value between a flow of the fluid discharged in the process that the film dressing is compressed onto the foam dressing, and a flow ($Q'2$) of the fluid discharged in the process that the film dressing and the foam dressing are compressed onto the surface of the wound site.

5. The wound volume measuring device according to claim 4, wherein said volume calculating part calculates the volume of said wound site by integrating the flow of said fluid measured until the negative pressure in said hermetically sealed space corresponds to a critical negative pressure.

6. The wound volume measuring device according to claim 4, further comprising
   a canister connected to said drain tube to receive the fluid discharged from said hermetically sealed space by the negative pressure.

7. The wound volume measuring device according to claim 4, further comprising
   a display part for displaying the volume of the wound calculated by said volume calculating part.

* * * * *